(12) United States Patent
Kobayashi et al.

(10) Patent No.: US 6,888,015 B2
(45) Date of Patent: May 3, 2005

(54) SPHINGOLIPID SYNTHESIS INHIBITOR

(75) Inventors: Shu Kobayashi, Tokyo (JP); Kentaro Hanada, Kanagawa (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/472,379

(22) PCT Filed: Apr. 19, 2002

(86) PCT No.: PCT/JP02/03934

§ 371 (c)(1),
(2), (4) Date: Sep. 23, 2003

(87) PCT Pub. No.: WO02/089784

PCT Pub. Date: Nov. 14, 2002

(65) Prior Publication Data

US 2004/0092600 A1 May 13, 2004

(30) Foreign Application Priority Data

May 1, 2001 (JP) .................................. 2001-133929

(51) Int. Cl.$^7$ ........................................... C07C 233/05
(52) U.S. Cl. ........................... 554/66; 554/35; 564/219; 564/223; 514/625; 514/629; 514/630
(58) Field of Search ..................... 554/35, 66; 564/219, 564/223; 514/625, 629, 630

(56) References Cited

U.S. PATENT DOCUMENTS 5,976,781 A * 11/1999 Haldar et al. ................... 435/4

OTHER PUBLICATIONS

Ueno et al, Tetrahedron Letters, vol. 42, 2001, pp 7863–7865.*

Fukusawa "Genetic evidence for ATP–dependent endoplasmic reticulum–to–Golgi apparatus trafficking of ceramide for sphingomyelin synthesis in Chinese hamster ovary cells" Journal of Cell Biology, v.144, No. 4, 1999, 673–685.

Hanada Both sphingolipids and cholesterol participate in the detergent insolubility of alkaline phosphatase, a glycosylphosphatidylinositol–anchored protein, in mammalian membranes Jrnl of Biological Chemistry, v.270, No 11, 1995, 6254–6260.

Funakoshi "Reconstitution of ATP– and cystosol–dependent transport of denovo synthesized ceramide to the site of sphingomylin synthesis in semi–intact cells" Journal of Biological Chemistry v. 275, No. 39, 2000, 29938–29945.

Rouser "Quantitative analysis of phospholipids by thinlayer chromatography and phosphorous analysis of spots" 1966 Lipids 1, 85–86.

Hanada "Selection of mammalian cell mutants in sphingolipis biosyntehsis" 2000, Methods in Enzymology 312, 304–317.

Hanada "Functional reconstitution of sphingomyelin synthase in Chinese hamster ovary cell membranes" 1991, Biochemica et Biophysica Acta 1086, 151–156.

Hanada "Purification of the serine palmitoyltransferase complex responsible for sphingoid base synthesis by using affinity–peptide chromatography techniques" Journal of Biological Chemistry v. 275, No. 12, 2000, 8409–8415.

Wang "Ceramide synthase" 1999, Method in Enzymology 311, 15–21.

Hanada "Mammalian cell mutants resistant to a sphingomylin–directed cytolysin: Genetic and biochemical evidence for complex formation of the LCB1 protein with the LCB2 protein for serine palmitoyltransferase" Journal of Biological Chemistry v. 273, No. 50, 1998, 33787–33794.

\* cited by examiner

Primary Examiner—Shailendra Kumar
(74) Attorney, Agent, or Firm—Sherman & Shalloway

(57) ABSTRACT

A inhibitor of sphingolipids synthesis comprising a compound represented by general formula A. Desirably, a novel inhibitor of sphingolipids synthesis comprising (1R, 3R) N-(3-hydroxy-1-hydroxymethyl-3-phenylpropyl) alkaneamide, wherein carbon number of alkanoyl group is 8–16.

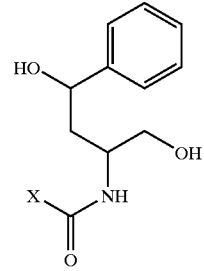

general formula A (in the formula, X is an aliphatic alkyl group, desirably is an aliphatic alkyl group having 7 to 15 carbon atoms).

6 Claims, 7 Drawing Sheets

|  | X |
|---|---|
| APBD-3 | CH$_3$CH$_2$- |
| APBD-8 | CH$_3$(CH$_2$)$_6$- |
| APBD-12 | CH$_3$(CH$_2$)$_{10}$- |
| APBD-16 | CH$_3$(CH$_2$)$_{14}$- |

A (2S,3R)-D-erythroceramid

B

C

D

SPHINGOLIPID SYNTHESIS INHIBITOR

FIELD OF THE INVENTION

The present invention relates to a novel of inhibitor of sphingolipids synthesis, particularly related to a novel inhibitor of sphingomyelin synthesis by selective inhibition of intracellular trafficking of ceramide.

BACKGROUND OF THE INVENTION

Sphingolipids are ubiquitous constituents of membrane lipids in mammalian cells and play various important roles in cell growth, differentiation, and apoptosis. Further, sphingolipids are involved in membrane trafficking and intracellular signaling as a factor requiring for the formation of membrane micro domains so called lipid rafts.

The biosynthesis process of sphingolipids in mammalian cells is supposed as follows. The first step is the condensation reaction of L-serine with palmitoyl CoA, said reaction is catalyzed by serine palmitoyl transferase and generates 3-ketodihydrosphingosine. Then, the obtained 3-ketodihydrosphingosine is reduced to dihydrosphingosine. Further, the obtained dihydrosphingosine undergoes N-acylation followed by desaturation to generate ceramide (Cer). These reactions to produce Cer occur at the cytosolic surface of the endoplasmic reticulum (ER). Then, Cer is delivered to the lumenal side of the Golgi apparatus and converted to sphingomyelin (SM) by SM synthase catalyzing transfer of phosphocholine from phosphatidylcholine (PC) to Cer. Cer is also converted to glucosylceramide (GlcCer) by GlcCer synthase catalyzing the transfer of glucose from uridine 5'-diphosphate (UDP)-glucose to Cer. The outline of the biosynthetic processes to SM or to GlcCer can be illustrated by the following schema.

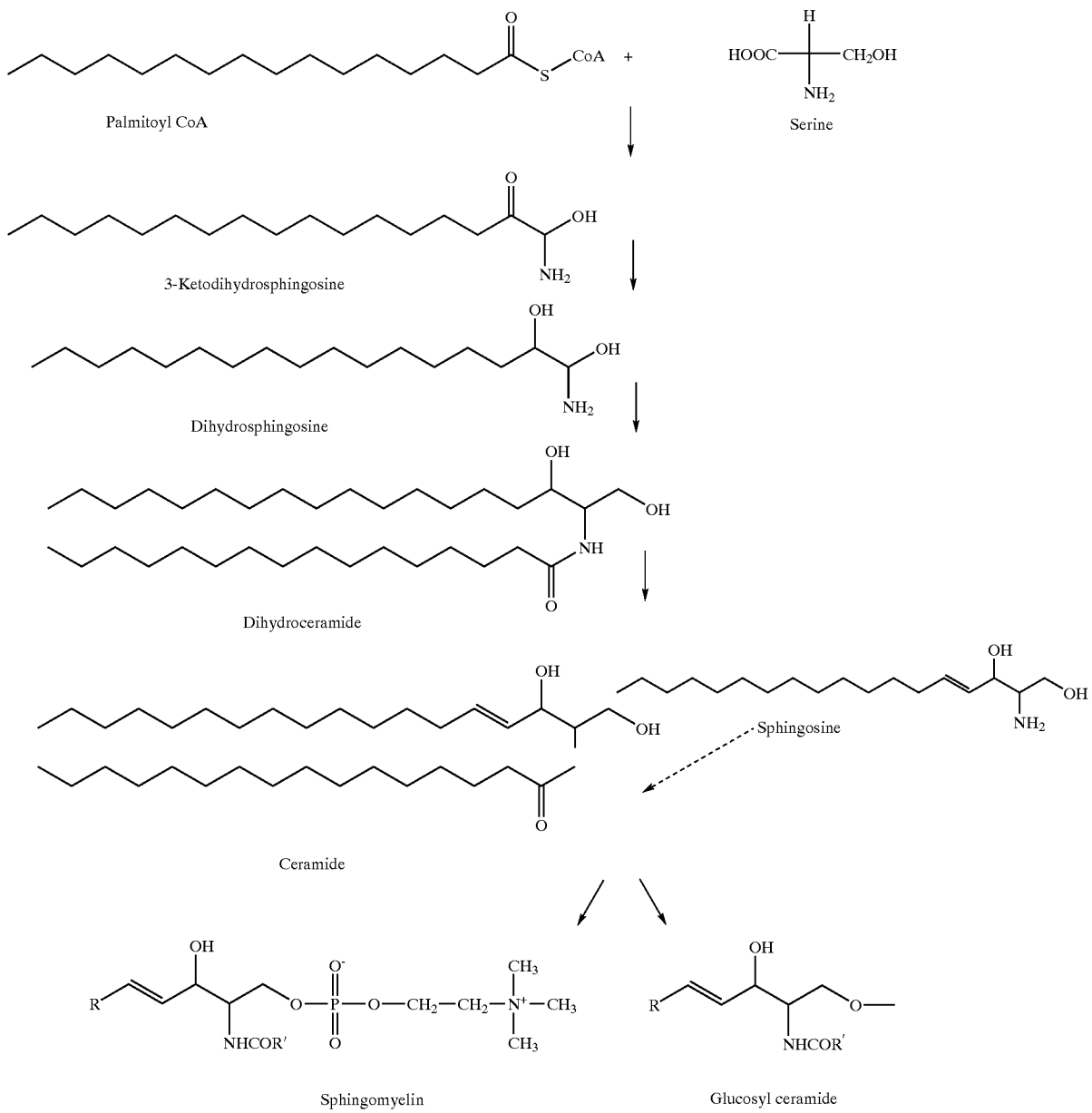

Inhibitors of specific steps of various processes (reaction, transferring or others) in de novo synthesis of sphingolipids should be useful means to investigate the metabolism and functions of sphingolipids in cultured cells and in living animals.

However, no specific inhibitor of SM synthesis in mammalian cells has been found so far. In addition, no drug that selectively inhibits intracellular trafficking of sphingolipids has been discovered.

Meanwhile, in Documents 1 and 2, the inventors of the present invention have analysed the wild-type Chinese hamster ovary (CHO) cell line and its mutant cell line, LY-A, defective in the pathway of Cer transport from the ER to the site of Golgi apparatus for the site of SM synthesis. These analyses have shown that the main pathway for transport of Cer from the ER to the site of SM synthesis is ATP-dependent. On the other hand, the access of Cer to the site of GlcCer synthesis is ATP-independent. These results have also shown that inhibition of transport of Cer from the ER to the site of SM synthesis causes inhibition of SM synthesis. However, no drug that selectively inhibits the intracellular trafficking of Cer is referred in Documents 1 and 2.

Therefore, the subject of the present invention is to provide a novel inhibitor which is selective to SM synthesis. Aiming to solve said subject, the inventors of the present invention have carried out various experiments using the compounds represented by the general formula A, and found out that there is a stereoisomer which inhibits selectively the synthesis of SM. And the subject of the present invention is accomplished.

DISCLOSURE OF THE INVENTION

The present invention is a novel inhibitor of sphingolipids synthesis comprising compounds represented by general formula A.

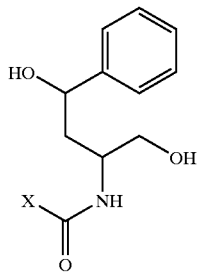

general formula A wherein, X is an aliphatic alkyl group.

Preferred are the inhibitors of sphingolipids synthesis belongs to above mentioned compounds represented by general formula A is (1R, 3R)N-(3-hydroxy-1-hydroxymethyl-3-phenylpropyl)alkaneamides having configuration indicated by following stereostructure, more preferred is the inhibitor of sphingolipids synthesis, wherein X of said chemical formula is an aliphatic alkyl group having 7 to 15 carbon atoms.

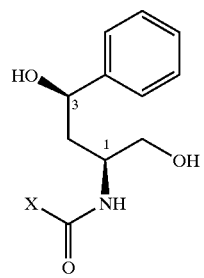

(1R, 3R)

BRIEF ILLUSTRATION OF THE DRAWINGS (A) of FIG. 1 shows four kinds of drugs having chemical structure of N(3-hydroxy-1-hydroxymethyl-3-phenylpropyl)alkaneamides (shortened to HPA) (APBD-3 whose carbon atom number of X is 2, APBD-8 whose carbon atom number of X is 7, APBD-12 whose carbon atom number of X is 11 and APBD-16 whose carbon atom number of X is 15). While, (B) of FIG. 1 shows effects of 2.5 $\mu$M drugs having different acyl chain lengths, namely, APBD-3, APDA-8, APDA-12, and APDA-16, on metabolic labeling of lipids with radioactive serine, compared to the drug-minus control (NONE). SM indicates the biological synthesis of sphingomyelin, GleCer indicates the biological synthesis of glucosyl ceramide, Cer indicates the biological synthesis of ceramide, and PS and PE indicate the biological formations of phosphatidylserine and phosphatidylethanolamine, respectively. In the drawings following to FIG. 1, these marks are same to FIG. 1.

(A) of FIG. 2 indicates the dose dependence of HPA-12 (corresponding to APBD-12) on inhibition of de novo synthesis of SM. (B) indicates the time course (up to 5 hours) of metabolic labeling of lipids with radioactive serine in the present (●) or absent (○) of 1 $\mu$M of HPA-12 (corresponding to APDD-12).

THE BEST EMBODIMENT TO CARRY OUT THE INVENTION

Figure 1:
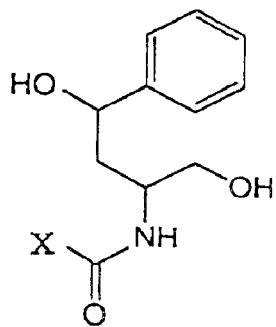
Figure 1:
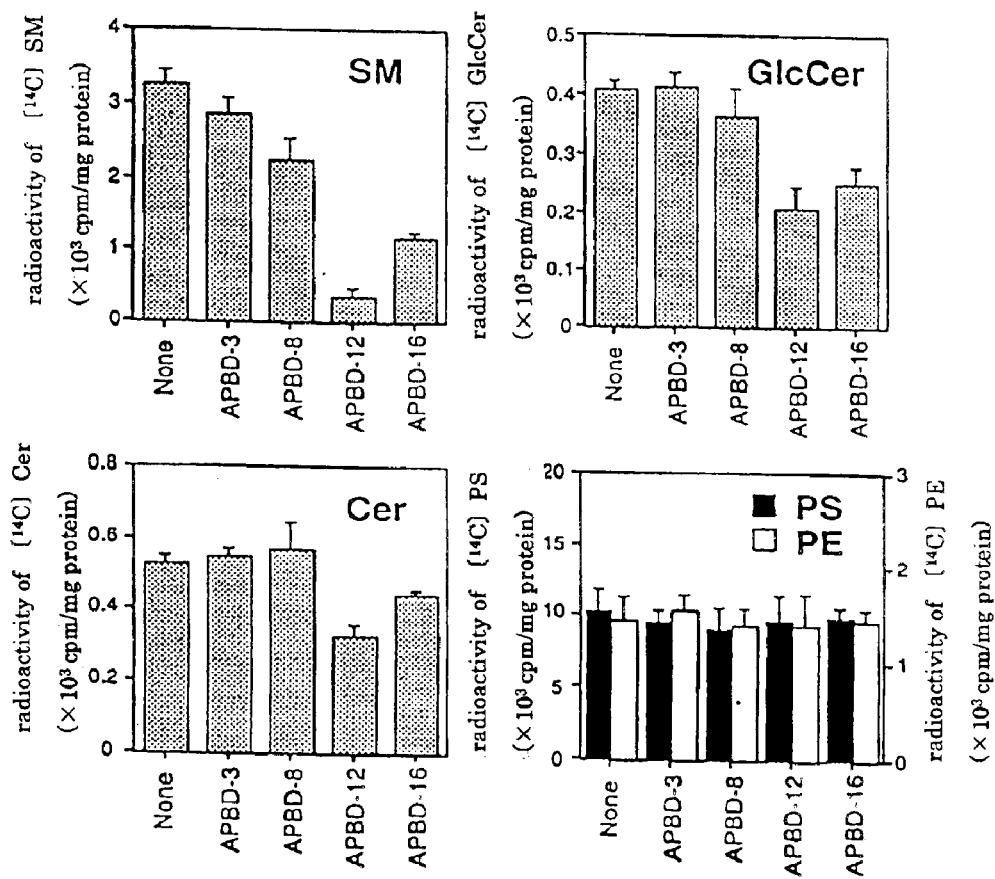

The present invention will be illustrated more in detail in accordance with the following description.

A. The compound which is useful as a novel inhibitor of biosynthesis of sphingolipids of the present invention and the method for synthesis thereof are illustrated as follows.

(1) Compound, N-(3-hydroxy-1-hydroxymethyl-3-phenylprol)alkaneamide (HPA) (wherein, alkane is an aliphatic group, desirably is an alkyl group having 7 to 10 carbon atoms)

(2) Synthesis of the compound depicted above;

Compound 1 whose hydroxyl group is protected by t-butyldimethylsilyl group (TBS) is reacted with dodecanoylchloride in $CH_2Cl_2$ solvent under the presence of amine which can be an accepter of HCl to obtain the compound 2 to an amino group of which a dodecanoyl group is introduced. Compound 2 is reacted with $(phenyl)_2CuLi$ in tetrahydrofuran (THF), to catty out the reaction that transforms thioester of SEt (ethylsilyl group) in compound 2 to ketone to obtain compound 3 which is replaced SEt of compound 2 by phenyl group. Then said protecting group TBS is removed under the presence of TBAF (tetrabutylammoniumfluoride) and N-(3-hydroxy-1-hydroxymethyl-3-phenylprol)dodecaneamide (HPA-12) is obtained. Above reactions can be illustrated by following schema 1.

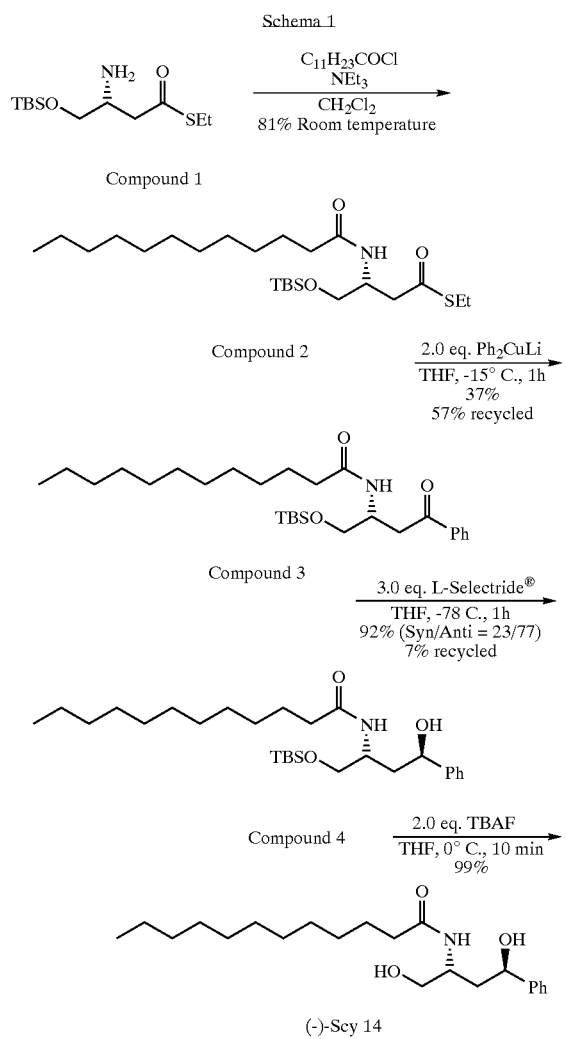

Schema 1

Compound 1

Compound 2

Compound 3

Compound 4

(-)-Scy 14

L-Selectride (™) is the 1.0 M tetrahydrofuran solution of Lithium tri-sec-butylborohydride.

The physical property of obtained HPA-12; $[\alpha]_D^{22}$ −35.1(c 0.80, $CHCl_3$);

Mp 75.5–77.0° C.; IR (KBr) 3293, 2919, 2849, 1643, 1551, 1493, 1054, 746 $cm^{-1}$; 1H NMR (400 MHz, $CDCl_3$): 0.88 (t, 3H, J=6.8 Hz), 1.26 (bs, 16H), 1.59 (bt, 2H, J=7.2 Hz), 1.92 (ddd, 1H, J=6.6, 8.5, 15.1 Hz), 2.03 (ddd, 1H, J=3.6, 5.7, 14.6 Hz), 2.15 (t, 3H, J=7.7 Hz), 3.65 (ddd, 1H, J=4.1, 11.3, 15.5 Hz), 4.01–4.08 (m, 1H), 4.79 (dd, 1H, J=3.4, 8.8 Hz), 6.48 (d, 1H, J=6.8 Hz), 7.23–7.36 (m, 5H); 13CNMR (100 MHz, $CDCl_3$): δ14.1, 22.7, 25.7, 29.3, 29.3, 29.3, 29.5, 29.6, 29.6, 31.9, 36.8, 40.7, 50.4, 65.5, 71.8, 125.5, 127.7, 128.5, 144.2, 174.3; HRMS calculated value: $C_{22}H_{37}NO_3(M^+)$ 363.2273, Experimental value 363.2279.

B. Investigation of mechanism as an inhibitor at the SM synthesis process of the compound represented by general formula A.

1. Experimental Materials for Aforementioned Investigation

L-[U-14C] serine (155 μmCi/mmol) and [methyl-14C] choline (55.0 mCi/mmol) are purchased from Amersham Pharmacia Biotech Co., Ltd. 6-[N-(7-nitrobenzo-2-oxa-1,3-diazol-4-yl)amino] caproyl-D-erythro-sphingosine (shortened to $C_6$-NBD-Cer) and N-(4,4-difluoro-5,7-dimethyl-4-bora-3a,4a-diaza-s-indacene-3-pentanoyl)-D-erythro-sphingosine (hereinafter shortened to $C_5$-DMB-Cer,) are purchased from Molecular Probe Inc. D-Erythro-[3-3H] sphingosine (20 Ci/mmol) is purchased from American Radiolabeled Chemicals Inc., D-erythro-sphingosine is purchased from Matraya Inc., fumonisin $B_1$, brefeldin A (BFA), and fatty acid-free bovine serum albumin (BSA) is purchased from Sigma Inc. Thin-layer chromatography (TLC) plate and high performance TLC plate (silica gel 60) is purchased from Merck Inc., dimethylsulfoxide (DMSO) is purchased from Wako Chemicals Co., Ltd. (Osaka, Japan), and 3-(4,5-dimethyl-2-thiazoyl)2,5-diphenyl-2H-tetrazoliumbromide (hereinafter shortened to MTT) is purchased from Dojin Chemical Laboratory.

2. Apparatus for Analysis:

For the image analysis of radioactive lipids separated on TLC plates, BAS 2000 or BAS 1800 image analyzer of Fuji Film Co., Ltd. is used. As a liquid scintillation detector, Model Ls3801 of Beckman Inc., and as a fluorescent spectrum analyzer, Model F-3000 of Hitachi Works Co., Ltd. is used. As a fluorescence microscope, Axiovert S100TV of Carl Zeiss Co., Ltd. is used.

3. Method for Cell Incubation

CHO-K1 cells and HeLa cells are purchased from American Type Cell Collection, and maintained by the inventors of the present invention. A CHO-K1 transformant stably expressing PLAP-HA, a chimera protein of placental alkaline phosphatase with the membrane-spanning domain of influenza hemagglutinin, was established and reported (Document 3) by the inventors of the present invention.

CHO cells are cultured in Ham's F12 medium supplemented with 10% newborn bovine serum (NBS), penicillin G (100 unit/mL) and streptomycin sulfate (100 μg/mL) at the temperature of 33° C. and 5% $CO_2$ atmosphere. In the case of HeLa cells, Dulbecco's minimum essential medium is used as a base medium instead of Ham's F12 medium.

Further, Nutridoma medium (Ham's F12 medium containing 1% Nutridoma-SP, product of Roche Molecular Biochemicals, and 25 μg/mL of gentamicin) is used as a serum-free medium. In the case when the medium is supplemented by DMSO or drugs dissolved in DMSO, the concentration of DMSO in culture medium is adjusted to be 0.01%.

4. Methods for Metabolic Labelling of Lipids with [14C] Serine and [14C] Choline;

CHO cells are seeded at the density of $1.0 \times 10^6$ cell in 5 mL of F12 medium containing 10% NBS, by per 60-mm dish, and cultured at 33° C. overnight. Then, the medium is changed to 1.5 mL of Nutridoma medium if necessary, various drugs are added and incubated at 4° C. for 15 minutes. Then, after addition of [14C] serine (0.75 μCi) or [14C] choline (1.0 μCi) to the medium, cells were incubated at 33° C. for various periods of time.

Cells are washed twice with 2 mL of cold phosphate-buffered saline (PBS), and lysed with 900 µL of 0.1% sodium dodecyl sulfate (SDS). Then, 800 µL and 20 µL of lysate are used for lipid extraction and determination of protein concentration, respectively.

For the analysis of lipids labeled with [$C^{14}$] serine, lipids were separated by TLC with a solvent consisting of methylacetate/n-propanol/chloroform/methanol/0.25%KCl (25:25:25:10:9, volume ratio) as a developing solvent.

For the analysis of the lipid labeled by [$^{14}C$] choline, the lipid is separated by one-dimensional TLC using chloroform/methanol/acetic acid/$H_2O$ (25:15:4:2, volume ratio) as a developing solvent. While, in the case of two-dimensional TLC, chloroform/methanol/acetic acid/$H_2O$ (65:25:4, volume ratio) is used for the first dimension and 1-butanol/acetic acid/$H_2O$ (60:20:20, volume ratio) is used for the second dimension as developing solvents.

Radioactive lipid separated on the TLC plates are detected with image analyzer depicted above. After the collection of gels from TLC plates by scraping, the radioactivity of each lipid is determined by liquid scintillation counting and normalized to the protein concentration of cells.

For the metabolic labeling by [$^{14}C$] serine in BFA-treated cells, the cells are preincubated with 1 µg/mL BFA in Nutridoma medium at 33° C. for 30 minutes, then, treated with or without 1 µM HPA-12 in the presence of 1 µg/mL BFA at 4° C. for 15 minutes prior to addition of [$^{14}C$] serine.

5. The Analytical Method of Metabolism of $C_5$-DMB-Cer in Intact Cells;

After CHO cells seeded in 60-mm dishes are cultured overnight, said CHO cells are labeled with 1 µM $C_5$-DMB-Cer in 1.5 mL of Nutridoma medium at 4° C. for 30 minutes. Then, after obtained said cells are washed 3 times with F12 medium, said cells are incubated in Nutridoma medium in the presence or absence of 2.5 µM HPA-12 for 15 minutes at 4° C., and then further incubated at 33° C. for various periods of time.

After washed with PBS, the chased cells are lysed with 0.1% SDS as mentioned above. The lipids extracted from cell lysate are separated by high performance TLC with a solvent of chloroform/methanol/$H_2O$ (volume ratio, 65:25:4). Quantitative measurement of $C_5$-DMB-SM and $C_5$-DMB-Cer are performed by scraping gel from TLC plates, extracting by chloroform/methanol/$H_2O$ (volume ratio, 1:2:0.8), and by measuring DMB fluorescence (excitation wave length 480 nm, emission wave length 515 nm) of the extracted product.

6. The Assay Method of Conversion of [$^3H$] Cer to [$^3H$] SM in Intact Cells.

The measurement of conversion of [$^3H$] Cer to [$^3H$] SM in cells is performed by a modified method of the method disclosed in Document 1. That is, as the first step, cells are pulse-labeled in 1.5 mL of Nutridoma medium containing 1 µM D-erythro-[$^3H$] sphingosine (2.5 µCi). After washed, the cells are incubated in 1.5 mL of Nutridoma medium supplemented with or without 1 µM HPA-12 at 4° C. for 15 minutes, then incubated under the presence of 100 µM fumonisin B, at 33° C. for various periods of time for chase.

The lipids are extracted from the chased cells, and separated by TLC with a developing solvent consisting of chloroform/methanol/$H_2O$ (volume ratio, 65:25:4). Then, the radioactivity of each lipid is measured by the method mentioned above.

7. The Method for Determination of Contents of Sphingolipids and Phospholipids in Cells CHO cells are seeded at density of 10×10$^6$ cells in 20 mL of F12 medium containing 10% NBS by per 150-mm dish, and incubated at 33° C. overnight. Then, after washed twice with 10 mL of serum-free F 12 medium, the cells are incubated in 20 mL of Nutridoma medium supplemented with or without 2.5 µM HPA-12 for 2 days. Each medium is replaced every 24 hours. After washed with PBS, the cells are harvested by scraping, and re-suspended in PBS. Then, lipids are extracted from the cells.

For analysis of phospholipids, extracted lipids are separated by TLC with a solvent of chloroform/methanol/acetic acid/$H_2O$ (volume ratio, 25:15:4:2).

Phosphorous contents in phospholipids are measured by the method disclosed in Document 4.

Contents of GlcCer and N-acetyl neuraminil lactosylseramide ($G_{M3}$) are determined by densitometric analysis of lipids stained with Coomassie Brilliant Blue disclosed in Document 5.

Cer contents are determined by using a sn-1,2-diacylglycerol assay reagent kit (Amersham Pharmcia Biotech).

8. Enzyme Assays

Membrane fraction prepared from CHO cells is used as an enzyme source.

Enzyme assays of SM synthesis and GlcCer synthase are carried out by using $C_6$-NBD-Cer as a substrate as disclosed in Document 6.

Serine palmitoyltransferase activity is determined by the method disclosed in Document 7, and sphingosine N-acyl transferase activity is determined by a modification of the method disclosed in Document 7.

9. Observations by Fluorescent Microscopy

After CHO cells grown on the glass coverslip (22-mm diameter) in 35 mm dishes are incubated in F12 medium containing 1 µM $C_5$-DMB-Cer at 4☐ for 30 minutes for pulse label, washed three times with 1 mL of F12 medium, and incubated in 1 mL of Nutridoma medium in the presence or absence of 2.5 µM HPA-12 at 4° C. for 15 minutes. Then, the pulse-labeled cells are incubated at 33° C. for 15 minutes for chase, washed with PBS containing 0.125% glutaraldehyde at 4° C. for 5 minutes. Immediately after the fixing, the specimens are observed and photographed under a fluorescent microscope.

10. Assay of Glycoprotein Transport from the ER to the Golgi Apparatus in Cells

The assay is carried out by the method disclosed in Document 1, by using a CHO-K1 transformant stably expressing PLAP-HA.

11. Assay of the Viability of Cells

CHO cells are seeded at a density of 2.0×10$^4$ per one hole of a 48-hole culture plate in 500 µL of F12 medium containing 10% NBS, and cultivated at 33☐ overnight. Then, the medium is changed to 500 µL of Nutridoma medium containing various concentrations of HPA compounds at 33° C. for 24 hours, and the viability of cells are determined using MTT as disclosed in Document 9.

12. Measurement of Protein Concentration

Measured by the BCA assay kit, which is the product available from Pierce Co., Ltd. BSA is used as the standard.

EXAMPLES

1. The effect of N-(3-hydroxy-1-hydroxymeyhyl-3-phenylpropyl) alkaneamides (HPA analogs; general formula A) on de novo synthesis of SM in CHO cells;

As shown in FIG. 1A, the effect of a series of N-(3-hydroxy- 1-hydroxymeyhyl-3-phenylpropyl)alkaneamides (APBD analogs, which are corresponding to HPA analogs), which are chemically synthesized compounds, on biosynthesis of sphingolipids in mammalian cells are examined.

The first of all, metabolic labeling of lipids with [$^{14}$C] serine in CHO cells is carried out in the presence of 2.5 μM HPA analogs. It is clearly understood from FIG. 1B that the formation of [$^{14}$C] SM is remarkably inhibited by HPA-12 among various HPA analogs having various acyl alkanes (HPA-3, HPA-8, HPA-12 and HPA-16 whose carbon atom number of N-acyl chain is 3, 8, 12 and 16 respectively). And it is also understood that the inhibitory effects of HPA-3, HPA-8 and HPA-16 on biosynthesis of sphingolipids are less than that of HPA-12.

While, at the concentration of 2.5 μM, according to the assays by said MTT reagents, these reagents do not affect the viability of cells.

Still more, since HPA-12 does not affect the formation of [$^{14}$C] phosphatidylserine (PS) and [$^{14}$C] phosphatidylethanolamine (PE), therefore inhibition of the formation of [$^{14}$C] SM by HPA-12 is not due to a non-specific dysfunction of lipid metabolism.

Figure 2:
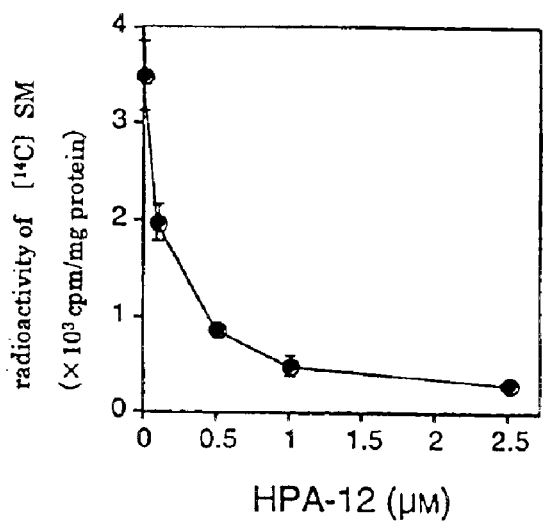
Figure 2:
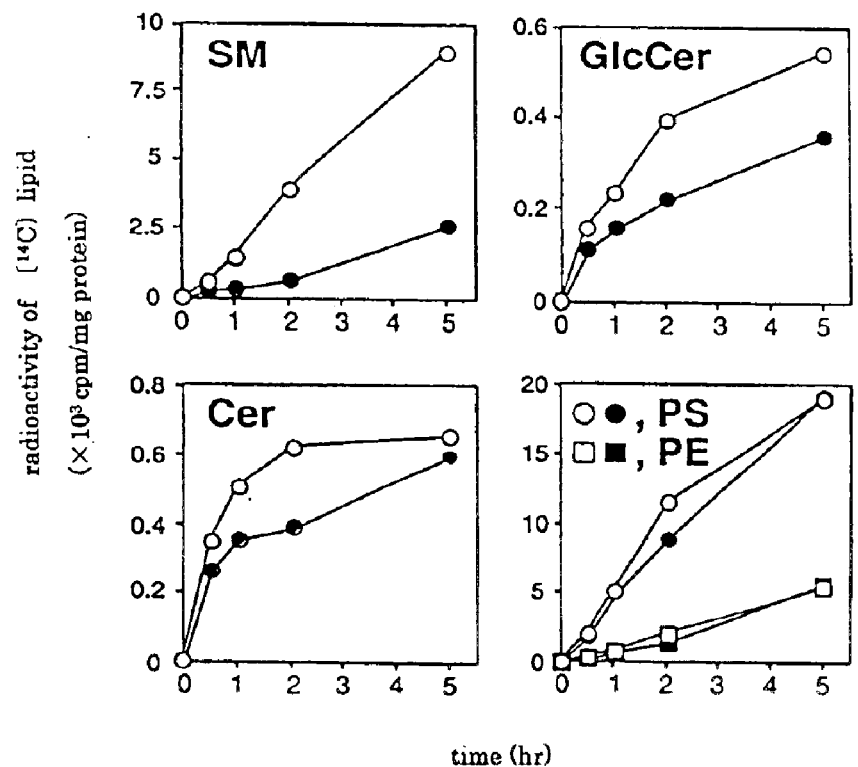

On 2-hour metabolic labeling of lipids with [$^{14}$C] serine, HPA-12 significantly inhibits the formation of [$^{14}$C] SM even at 0.1 μM, and the inhibitory effect reaches a plateau around 1 μM (FIG. 2A).

HPA-12 at 10 μM is highly toxic to CHO cells (concrete data are not shown), not allowing to carry out the metabolic labeling experiments at more than 10 μM of the drug. The time course of metabolic labeling up to 5 hours shows that 1 μM HPA-12 inhibits the formation of [$^{14}$C] to approximately 30% of the drug-free control level throughout the incubation period (FIG. 2B).

The formation of [$^{14}$C] Cer and [$^{14}$C] Glc in metabolic labeling with [$^{14}$C] serine is also significantly inhibited by HPA-12, however, the inhibitory effects on GlcCer and Cer synthesis are weaker than the inhibitory effect on SM synthesis (FIG. 2B). As reported in the published Document 1, when the conversion from Cer to SM is inhibited, it is supposed that de novo synthesis of sphingosine bases is repressed by an unknown mechanism. Therefore, the slight inhibition of the formation of Cer and GlcCer from [$^{14}$C] serine by HPA-12 likely results from a secondary effect of the inhibition of conversion from Cer to SM.

Figure 3:
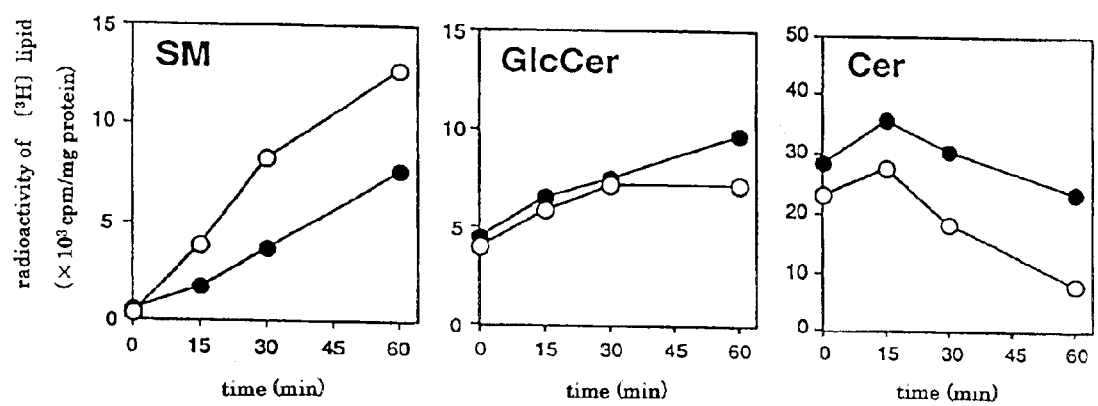
FIG. 3 shows the effects of HPA-12 on the conversions from Cer to SM and to GlcCer in living cells.

2. The inhibitory effect of HPA12 on conversion of Cer to SM in intact cells;

To examine the inhibitory effect of HPA-12 on the step of Cer-to-SM conversion specifically, metabolic labeling experiments with [$^3$H] sphingosine are carried out. When cells are labelled with [$^3$H] sphingosine at 15° C., [$^3$H] sphingosine is effectively N-acylated and converted to [$^3$H] Cer, but, [$^3$H] Cer is not converted to [$^3$H] SM at this temperature (Document 2). After the labeling with [$^3$H] sphingosine at low temperature to generate [$^3$H] Cer, the cells are treated with 1 μM HPA-12 at 4° C. for 15 minutes, and then incubated at 33° C. up to 1 hour for chase. During the chase, de novo synthesis of [$^3$H] Cer from [$^3$H] sphingosine is blocked by fumonisin B$_1$, which is an inhibitor of sphingosine N-acyltransferase. Under these chase conditions, 1 μM HPA-12 inhibits the formation of [$^3$H] SM by 50%, whereas it does not inhibit and rather increases the formation of [$^3$H] GlcCer (FIG. 3, ● shows the case when 1 μM HPA-12 is added). These results indicate that HPA-12 inhibits conversion of Cer to SM, but to GlcCer, in intact cells.

3. Effect of HPA-12 on biosynthesis of phosphatidylcholine

Figure 4:
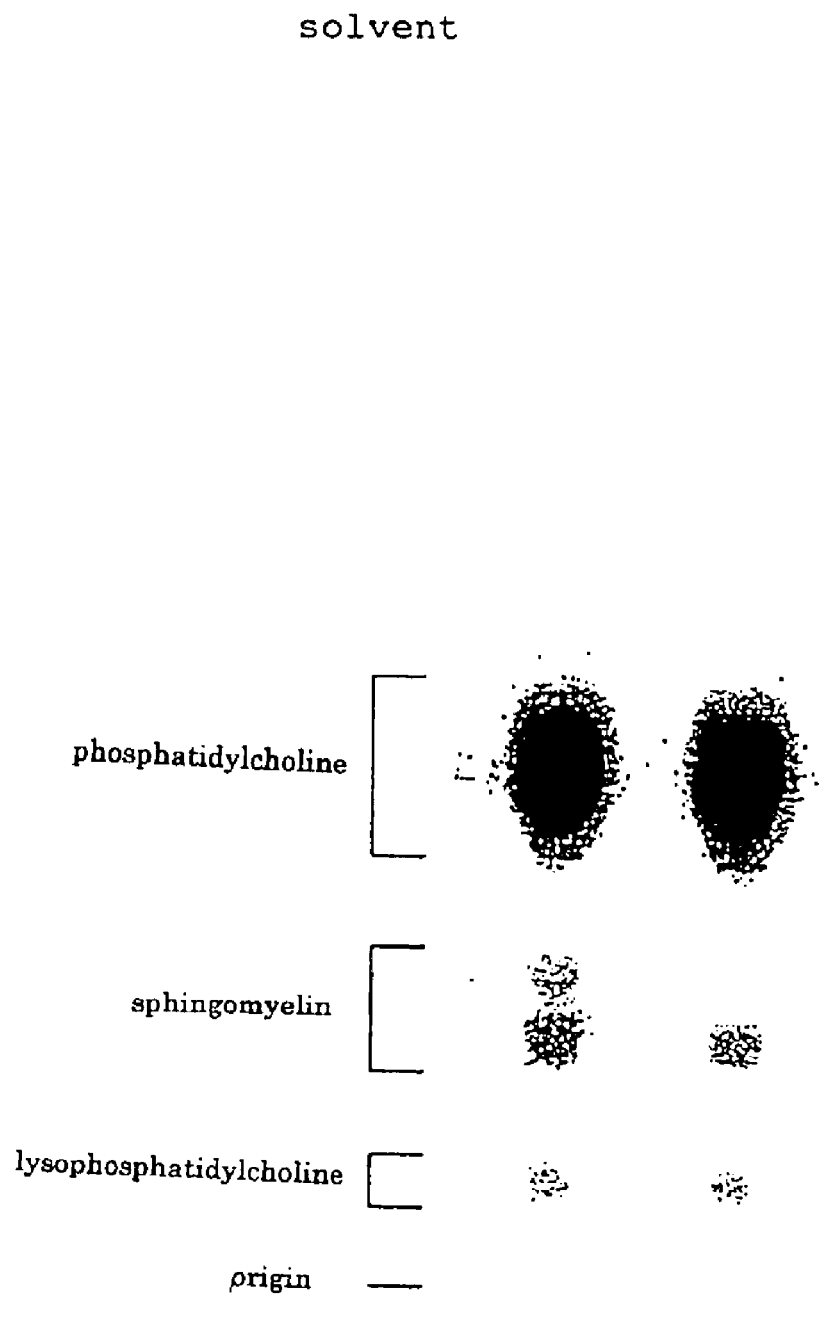
FIG. 4 shows the effect of HPA-12 on the synthesis of phosphatidylcholine (PC).

SM is synthesized by the transfer of phosphocholine from phosphatidylcholine (PC) to Cer, and this reaction is catalyzed by SM synthase. To examine the possibility that inhibition of Cer-to-SM conversion by HPA-12 is due to inhibition of PC synthesis, metabolic labeling of lipids with [$^{14}$C] choline is carried out (FIG. 4). When cells are incubated with [$^{14}$C] choline at 33° C. for 4 hours in presence or absence of 1μM HPA-12, the levels of [$^{14}$C] PC are almost equal between the drug-treated and untreated cells, but the level of [$^{14}$C] SM in the drug-treated cells is about half of the drug-untreated control level.

Judging from said results, the possibility mentioned above, that is, inhibition of conversion of Cer to SM by HPA-12 might be caused by inhibition of PC synthesis is ruled out.

4. Evidence for that HPA-12 is not converted to choline-containing metabolites;

No radioactive bands specifically produced only in the presence of HPA-12 are observed in TLC patterns of [$^{14}$C] choline labeled lipids of one dimentional (FIG. 4) nor two dimensional analysis (concrete data are not shown). Therefore, it is deemed that HPA-12 itself is not converted to any choline-containing metabolites.

5. Reduction of the content of SM in cells by HPA-12;

To examine whether HPA-12 actually affects the content of SM in cells, cells are cultured in Nutridoma medium in the presence or absence of 2.5 μM HPA-12 for two days, and then, chemical amounts of various lipids in cells are quantitatively determined. The obtained results are summarized in Table 1.

TABLE 1

| HPA-12 | composition of phospholipids | | | | $G_{M3}$ nmol/mg protein | GlcCer nmol/mg protein | Cer nmol/mg protein |
|---|---|---|---|---|---|---|---|
| | SM | PC | PI/PS | PE | | | |
| | % of total lipids recovered | | | | | | |
| none | 12.0 ± 0.1 | 43.3 ± 0.1 | 13.2 ± 0.4 | 31.5 ± 0.2 | 7.1 ± 0.5 | 0.9 ± 0.1 | 0.45 ± 0.04 |
| 2.5□M | 8.4 ± 0.1 | 47.5 ± 0.2 | 13.4 ± 0.3 | 30.6 ± 0.3 | 8.5 ± 0.8 | 1.4 ± 0.1 | 0.40 ± 0.13 |

HPA-12 does not affect levels of total phospholipids. The contents of total phospholipids in the drug-untreated and drug-treated cells are 288±3 nmol/mg protein and 315±2 nmol/mg protein respectively. However, the content of SM in HPA-12 treated cells is lower by 30% than the drug-free control level. The reduced amount of SM in HPA-12 treated cells seems to be compensated by an increase of PC (Table 1). In contrast, HPA-12 treatment causes an increase in contents of GlcCer and $G_{M3}$ to 150% and 120%, respectively, of the drug-untreated control levels (Table 1). There is no significant difference in the content of ceramide between the two (Table 1). These results consist with the conclusion showed above stating that HPA-12 inhibits the conversion of Cer to SM, but not to GlcCer.

6. Evidence for that HPA-12 is neither an inhibitor of SM synthesis nor of other key enzymes for sphingolipid synthesis;

It is examined whether HPA-12 inhibits the activities of SM synthase and GlcCer synthase from CHO cells membrane fraction, by using a fluorescent Cer analogue, $C_6$-NBD-Cer, as the enzyme substrate. Neither of SM synthase nor GlcCer synthase is inhibited by HPA-12, even when exposed to a high concentration (20 $\mu$M HPA-12 (Table 2). Further, inhibition of SM synthase activity is not observed either when $C_5$-DMB-Cer is used as the enzyme substrate (experimental data are not shown).

In addition, 20 $\mu$M HPA-12 does not affect activitis of serine palmitoyltransferase and sphingosine N-acyl transferase in the membrane fraction prepared from CHO cells (experimental data are not shown).

Therefore, HPA-12 is not an inhibitor on these key enzymes involved in de novo SM synthesis.

TABLE 2

| HPA-12 | $C_6$-NBD-SM | $C_6$-NBD-GlcCer |
|---|---|---|
| | pmol/mg protein/10 minutes | |
| none | 171.5 ± 6.9 | 354.2 ± 24.8 |
| 20 $\mu$M | 168.1 ± 1.7 | 325.9 ± 17.1 |

7. The effect of HPA-12 on SM synthesis in BFA-treated cells;

The possibility that HPA-12 affects transport of Cer from ER to the site of SM synthesis is examined. If this possibility is correct, one can predict that fusion of the ER, in which Cer synthase exists, and the Golgi apparatus, in which SM synthase exists, by BFA treatment, suppresses the inhibitory effect of HPA-12 on the formation of SM in the cells.

Figure 5:
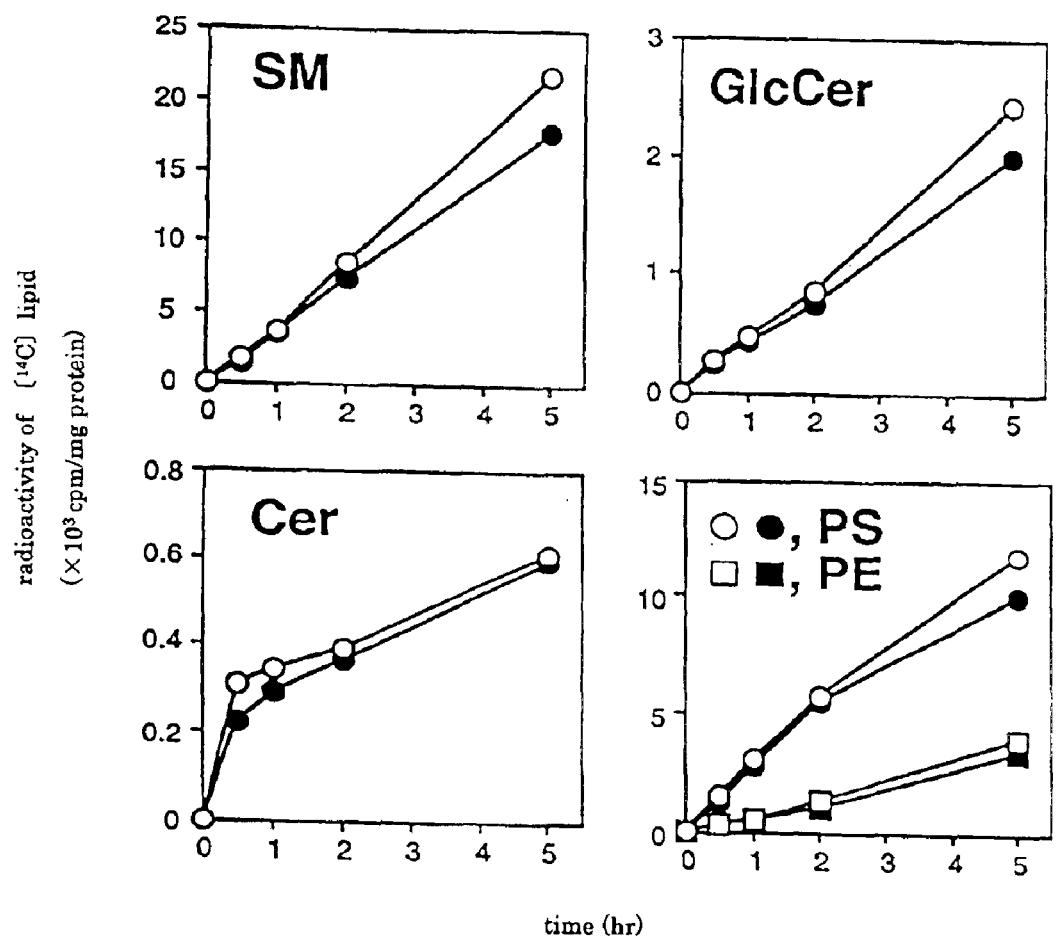
FIG. 5 shows the effect of HPA-12 on SM synthesis in cells, in which the ER and the Golgi apparatus are merged.

In fact, when the ER is fused with the Golgi apparatus by treatment of cells with BFA, 1 $\mu$M HPA-12 no longer inhibits the formation of [$^{14}$C] serine-derived SM (FIG. 5).

These results support the notion that HPA-12 inhibits trafficking of Cer from the ER to the site where SM synthase exists.

8. The effects of HPA-12 on intracellular redistribution and metabolism of $C_5$-DMB-Cer;

The inventors of the present invention have already reported that the activity of ATP-dependent transport of natural ceramide from the ER to the Golgi apparatus can be qualitatively assessed from analysis of redistribution of $C_5$-DMB-Cer, a fluorescent Cer analog, from the ER to the Golgi apparatus (Document 1). To explore the possibility that HPA-12 inhibits Cer transport, the effect of HPA-12 on the behavior of $C_5$-DMB-Cer in CHO cells is examined.

For pulse labeling of various intracellular membranes including the ER, cells are incubated with $C_5$-DMB-Cer at 4° C. for 30 minutes, and incubated in the presence or absence of 2.5 $\mu$M HPA-12 at 4° C. for further 15 minutes. Then the pulse-labeled cells are chased at 33° C. for 15 minutes for redistribution of $C_5$-DMB-Cer. Before the chase, HPA-12-treated and untreated cells show essentially the same pattern of intracellular DMB-fluorescence distributing throughout intracellular membranes. In contrast, when the pulse-labeled cells are chased, accumulation of DMB-fluorescence to the perinuclear Golgi region is clearly lower in HPA-12-treated cells than in the untreated control cells. This inhibition of $C_5$-DMB-Cer redistribution is consistent with inhibition of conversion of $C_5$-DMB-Cer to $C_5$-DMB-SM by 50% in HPA-12 treated cell (experimental data are not shown).

9. Identification of a specific stereoisomer of HPA-12 which inhibits the transport of Cer;

HPA-12 has two chiral carbon atoms at C-1 and C-3-positions. Therefore, it includes four stereoisomes, which are represented by (1S, 3R), (1R, 3S), (1R, 3R) and (1S, 3S) as mentioned below.

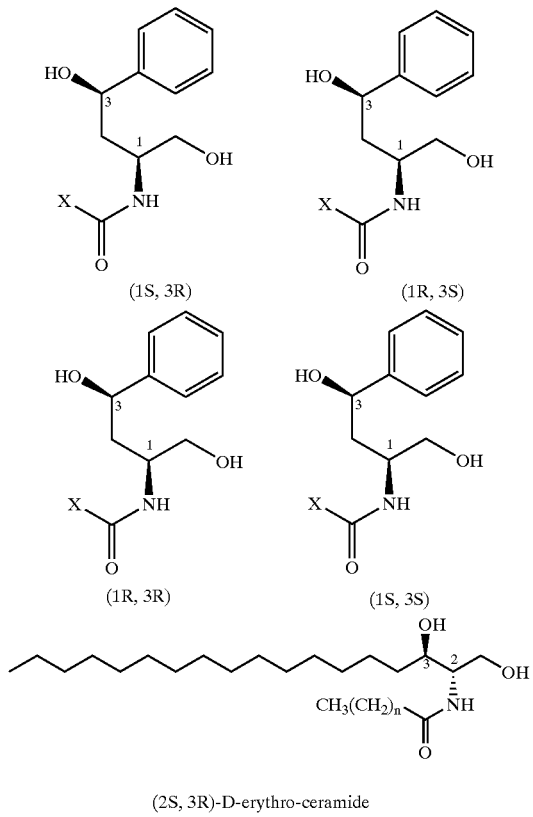

Among formulae mentioned above, (2S, 3R)-D-erythro-ceramide is the structural formula of natural ceramide.

It is determined whether the activity of HPA-12 to inhibit SM formation is attributed to a specific stereoisomer or not.

For this, the four stereoisomers are first divided into two subgroups, one contains (1R, 3R) and (1S, 3S)-HPA-12 (a), and another contains (1S, 3R) and (1R, 3S)-HPA-12 (b). The two groups are chemically synthesized, and their activities are examined in metabolic labeling with [$^{14}$C] serine. Only the former subgroup (a) strongly inhibits SM synthesis (FIG. 6B).

Next, (1R, 3R)-HPA-12 and (1S, 3S)-HPA-12 are separately synthesized, and their activities are examined. The (1R, 3R) type inhibits de novo synthesis of SM strongly, whereas (1S, 3S) does moderately (FIG. 6B).

Figure 6:
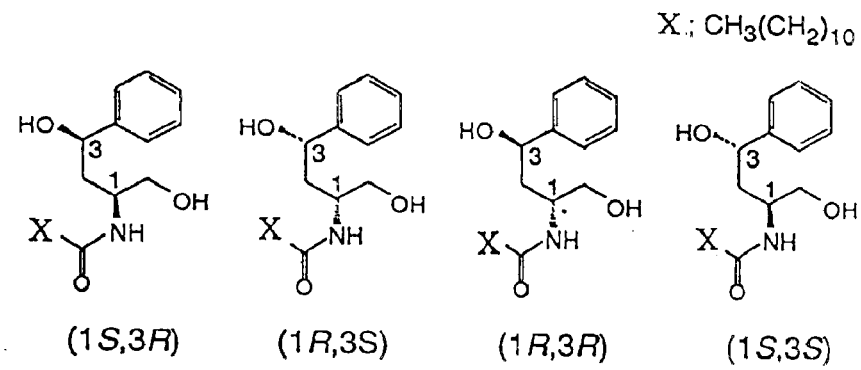
FIG. 6 shows four stereoisomers of HPA-12 and the structures of the natural (2S, 3R)-D-erythro-ceramide (A), and shows the relationship between stereostructure of HPA-12 and the inhibitory effect on de novo biosynthesis of SM (B, C), and shows the effect of (1R, 3R)-HPA-12 (D) as an inhibitor of de novo synthesis of SM in HeLa cells.
Figure 6:
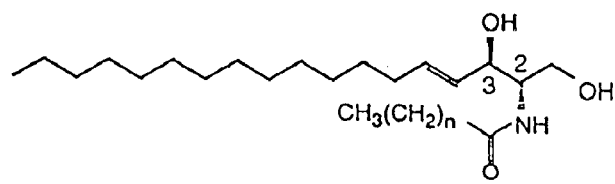
Figure 6:
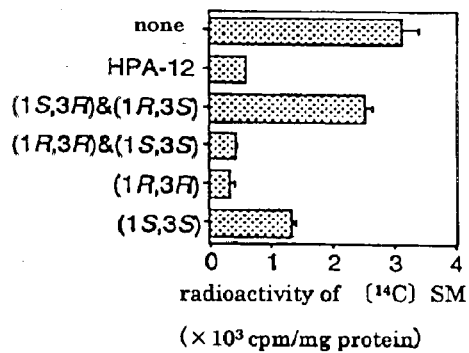
Figure 6:
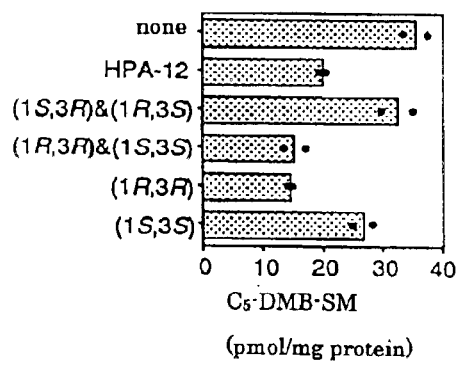
Figure 6:
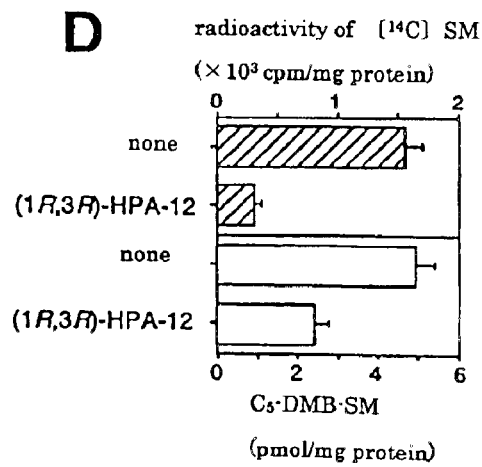

A similar pattern of structure and activity relationship is observed on conversion of $C_5$-DMB-Cer to $C_5$-DMB-SM in intact cells (FIG. 6C).

Further, (1R, 3R)-HPA-12 inhibits synthesis of SM in HeLa cells. (FIG. 6D).

These results indicate that, among four streoisomers of HPA-12, the (1R, 3R) type has the strongest inhibitory activity on the Cer-to-SM conversion, and that (1R, 3R)-HPA-12 has the activity not only in CHO cells but also in other mammalian cell types.

Figure 7:
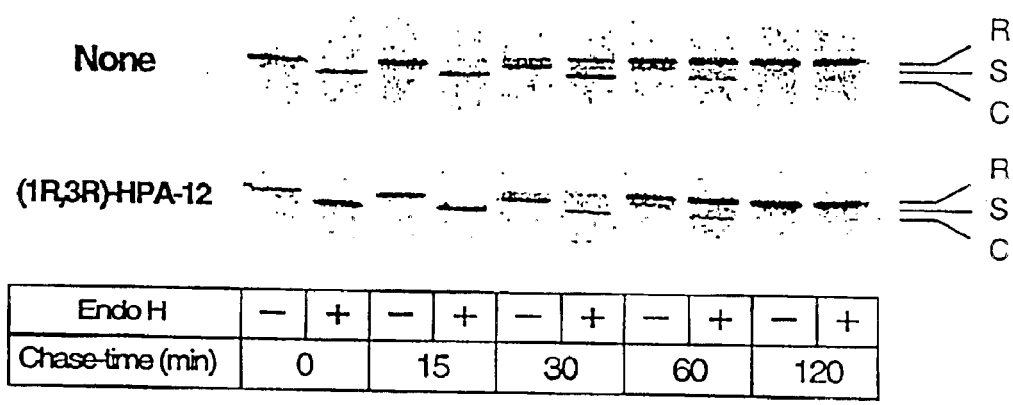
FIG. 7 shows the effect of (1R, 3R)-HPA-12 on the activity of protein trafficking from the ER to the Golgi apparatus.

10. Effect of (1R, 3R)-HPA-12 on protein transport from the ER to the Golgi apparatus;

The effect of (1R, 3R)-HPA-12 on glycoprotein transport from the ER to the Golgi apparatus are examined by using CHO-K1 transformant cells which stably express PLAP-HA, a chimera protein of placental alkaline phosphatase with the membrane spanning domain of influenza hemagglutinin. The maturation of sugar chains of PLAP-HA, which is newly synthesized in the ER, to an endoglycosidase H (EndoH)-resistant form by a sugar chain modifying enzyme which is localized to Golgi apparatus, is defined as an index of the arrival to the Golgi apparatus. The maturation rate of newly synthesized PLAP-HA to an EndoH-resistant form is not affected by 2.5 μM (1R, 3R)-HPA-12 (FIG. 7: from the comparison to untreated control=None). In FIG. 7, R, S, and C mean resistant, sensitive, and cleavage forms, respectively. The time course of form changing during the chase is shown in FIG. 7 (chase-time, minute). According to the results, it is understood that (1R, 3R)-HPA-12 does not inhibit protein trafficking from the ER to the Golgi apparatus.

Industrial Applicability

As mentioned above, the compounds represented by general formula A bring an excellent effect to inhibit selectively a trafficking route of Cer to the site of SM synthesis.

The List of Reference Documents Cited in the Specification

Document 1:
Masayoshi Fukusawa, Masahiro Nishijima and Kentaro Hanada (1999), "Genetic evidence for ATP-dependent endoplasmic reticulum-to-Golgi apparatus trafficking of ceramide for sphingomyelin synthesis in Chainese hamster ovary cells" Journal of Cell Biology 144, 673–685.

Document 2:
Kentaro Hanada, Masahiro Nishijima, Yuzuru Akamatsu and Richard E. Pagano (1995) "Both sphingolipids and cholesterol participate in the detergent insolubility of alkaline phosphatase, a glycosylphosphatidylinositol-anchored protein, in mammalian membranes" Journal of Biological Chemistry 270, 6254–6260.

Document 3:
Tomoko Funakoshi, Satoshi Yasuda, Masayoshi Fukasawa, Masahiro Nishijima and Kentaro Hanada (2000) "Reconstitution of ATP-and cytosol-dependent transport of denovo synthesized ceramide to the site of sphingomylin synthesis in semi-intact cells" Journal of Biological Chemistry 275, 29938–29945.

Document 4:
Gerge Rouse, A. N. Siakotos and Sidney Fleicher (1966) "Quantitative analysis of phospholipids by thin-layer chromatography and phosphorus analysis of spots" Lipids 1, 85–86.

Document 5:
Kentaro Hanada and Masahiro Nishijima (2000) "Selection of mammalian cell mutants in sphingolipis biosyntehsis" Methods in Enzymology 312, 304–317.

Document 6:
Kentaro Hanada, Mio Horii and Yuzuru Akamatsu (1991) "Functional reconstitution of sphingomyelin synthase in Chinese hamster ovary cell membranes" Biochemica et Biophysica Acta 1086, 151–156.

Document 7:
Kentaro Hanada, Tomoko Hara and Masahiro Nishijima (2000) "Purification of the serine palmitoyltransferase complex responsible for sphingoid base synthesis by using affinity-peptide chromatography techniques" Journal of Biological Chemistry 257, 8409–8415.

Document 8:
Elaine Wang and alfred H. Mellill. Jr. (2000) "Ceramide synthase" Method in Enzymology 311, 15–21.

Document 9:
Kentaro Hanada, Tomoko Hara, Masayoshi Fukusawa, Akiko Yamaji, Masato Umeda and Masahiro Nishijima (1998) "Mammalian cell mutants resistant to a sphingomylin-directed cytolysin: Genetic and biochemical evidence for complex formation of the LCB1 protein with the LCB2 protein for serine palmitoyltransferase" Journal of Biological Chemistry 273, 33783–33794.

We claim:

1. A compound of general formula A,

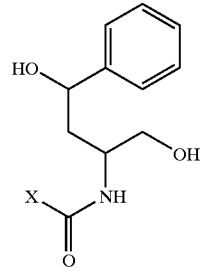

general formula A wherein, X is an aliphatic alkyl group.

2. The compound as claimed in claim 1, wherein a compound represented by general formula A is (1R, 3R) N-(3-hydroxy- 1-hydroxymethyl-3-phenylpropyl) alkaneamides having steric structure represented by following chemical formula

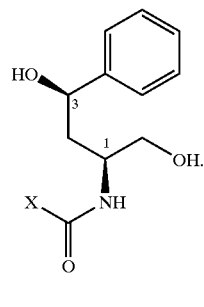

(1R, 3R)

3. The compound as claimed in claim 2, wherein X of the chemical formula is an aliphatic alkyl group having 7 to 15 carbon atoms.

4. A novel inhibitor of sphingolipid synthesis comprising the compound as claimed in claim 1.

5. A novel inhibitor of sphingolipid synthesis comprising the compound as claimed in claim 2.

6. A novel inhibitor of sphingolipid synthesis comprising the compound as claimed in claim 3.

* * * * *